United States Patent [19]

Chan et al.

[11] Patent Number: 5,129,954
[45] Date of Patent: Jul. 14, 1992

[54] BETA-HYDROXYESTERS FOR USE AS VANILLIN-RELEASE ADDITIVES IN SMOKING COMPOSITIONS

[75] Inventors: W. Geoffrey Chan, Chesterfield; Yoram Houminer, Richmond; John B. Paine, III, Richmond; Kenneth F. Podraza, Richmond, all of Va.

[73] Assignees: Philip Morris Incorporated, New York, N.Y.; Philip Morris Products Inc., Richmond, Va.

[21] Appl. No.: 537,775

[22] Filed: Jun. 13, 1990

[51] Int. Cl.$^5$ .......................... A24B 3/12; C07C 69/76
[52] U.S. Cl. .................................................. 131/276
[58] Field of Search ................. 131/276; 560/103, 106

Primary Examiner—V. Millin
Attorney, Agent, or Firm—James E. Schardt; George A. Depaoli

[57] ABSTRACT

This invention provides novel β-hydroxyesters which have utility as a flavorant-release additive in smoking compositions.

Under cigarette smoking conditions, a combustible filler and/or paper wrapper additive such as ethyl 3-hydroxy-3-(4'-hydroxy-3'-methoxyphenyl)-2-phenyl-propanoate pyrolyzes into vanillin and ethyl phenylacetate flavorants as volatile components of the cigarette smoke.

27 Claims, No Drawings

BETA-HYDROXYESTERS FOR USE AS VANILLIN-RELEASE ADDITIVES IN SMOKING COMPOSITIONS

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,9811; 3,914,451; 3,915,175; 3,920,027; 3,924,644; 3,937,228; 3,943,943; 3,586,387; 3,379,754; and the like.

J. C. Leffingwell et al "Tobacco Flavoring For Smoking Products" (R. J. Reynolds publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. No. 3,332,428 and U.S. Pat. No. 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,177,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

U.S. Pat. Nos. 4,473,085 and 4,607,118 describe β-hydroxyesters which as additives in smoking compositions pyrolyze into volatile ketone and ester flavorants under smoking conditions.

Of specific interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethyl vanillyl-D-glucoside yields ethyl vanillin and levoglucosan as pyrolysis products.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel β-hydroxyester compounds which are adapted to be incorporated into cigarette filler and/or paper wrapper components, and which under normal smoking conditions release volatile ester and vanillin flavorants into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

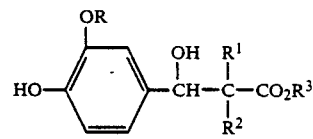

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

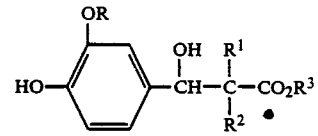

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

Illustrative of $C_1$–$C_4$ alkyl substituents in the above represented flavorant-release additive formula are methyl, ethyl, propyl, 2-propyl, butyl, 2-butyl and isobutyl groups.

Illustrative of $C_6-C_{10}$ aromatic substituents are phenyl, tolyl, xylyl, benzyl, phenylethyl, methoxyphenyl, and the like.

A cigarette smoking product in accordance with the present invention typically contains between about 0.01–5 weight percent of flavorant-release additive in the paper wrapper, based on the weight of combustible filler.

In a further embodiment an invention cigarette product contains between about 0.01–5 weight percent of flavorant-release additive in the paper wrapper, and contains between about 0.0001–5 weight percent of flavorant-release additive in the combustible filler, based on the weight of filler.

A present invention flavorant-release additive which is incorporated in smoking compositions as described above is a low volatility compound which under normal smoking conditions pyrolyzes into two volatile constituents, both of which enhance the flavor and aroma of low delivery cigarette smoke:

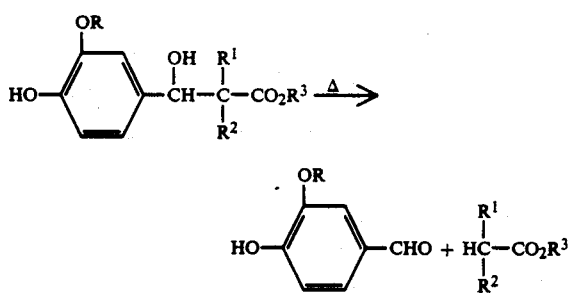

where R, $R^1$, $R^2$ and $R^3$ are as previously defined.

An important feature of an invention smoking composition is the release of two flavorants under smoking conditions, one of which is an ester and the other is vanillin or ethyl vanillin.

Both the ester and vanillin volatiles which are released have exceptional organoleptic properties. Each of the compounds contributes a pleasant flavor and aroma to cigarette smoke.

Preparation Of Flavorant-release Compounds

One method of preparing the invention β-hydroxyester flavorant-release compounds is by the reaction of an alkanoate derivative with an aldehyde derivative, both of which derivatives are appropriately substituted as previously defined:

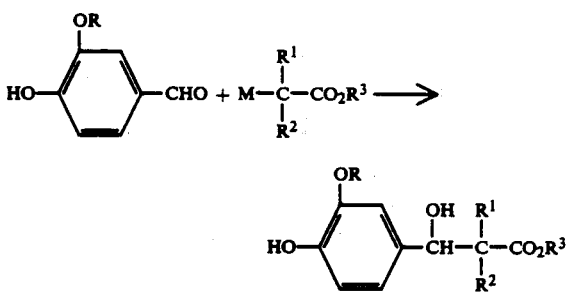

where M is a monovalent metal atom such as lithium, sodium or potassium.

The reaction is conducted in the presence of a strong base such as lithium diisopropylamide or alkali metal hydride.

In a typical procedure the base is added to the alkanoate in an inert solvent medium such as tetrahydrofuran or dimethylformamide, maintained at a temperature between about −80° C. and 50° C. under an inert atmosphere. A disadvantage of the above described synthesis procedure is the interaction of the phenolic hydroxyl group with the strong base, and the loss of starting material by precipitation from solution.

As an improved method of synthesis to achieve a high yield of final product, this invention provides a process for preparing a β-hydroxyester corresponding to the formula:

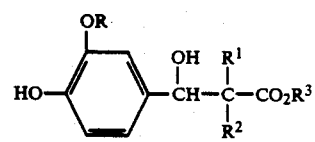

which comprises (1) condensing the following reagents under Claisen condensation conditions in an organic solvent medium:

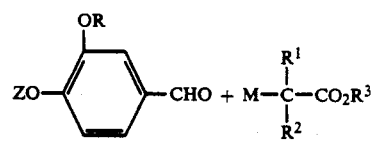

to form an intermediate corresponding to the formula:

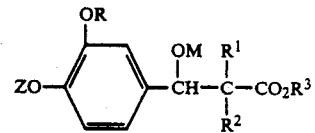

and (2) converting the —OZ and —OM substituents to hydroxyl groups by hydrolysis or hydrogenolysis means; wherein in the above represented formulae R is methyl or ethyl; $R^1$ is hydrogen or a $C_1-C_4$ alkyl substituent; $R^2$ is hydrogen or a $C_1-C_4$ alkyl or $C_6-C_{10}$ aromatic substituent; $R^3$ is a $C_1-C_4$ alkyl or $C_6-C_{10}$ aromatic substituent; M is a monovalent metal atom which is displaced by hydrogen under acidic hydrolysis conditions; and Z is a $C_1-C_{10}$ organic radical which is displaced by hydrogen under hydrogenation or acidic hydrolysis conditions.

The condensation reaction in step (1) is conducted at a temperature in the range between about −80° C. and 50° C. in a solvent medium such as tetrahydrofuran or diethyl ether. After completion of the condensation reaction in a time period between about 1–5 hours, the product medium is quenched with an acidic solution. It is essential to maintain acidic conditions during the neutralization and product recovery procedure as demonstrated in Example IV. Under aqueous basic conditions, the β-hydroxyester product undergoes a relatively fast retro-aldol reaction which causes a substantial loss of product yield.

The $C_1-C_{10}$ organic radical represented by Z in the above formulae is a phenol-protective group which is displaced by hydrogen under hydrogenation or acidic hydrolysis conditions. The Z radical can be any organic structure which is susceptible to chemical reaction, as illustrated by the Z groups represented in Examples IV–VII.

Preparation Of Tobacco Compositions

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to the formula:

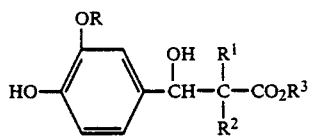

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituted.

The invention β-hydroxyester flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously descried hereinabove, an invention flavorant-release additive also can be incorporated in the paper wrapper of cigarette products, for the purpose of enhancing the aroma of cigarette sidestream smoke under smoking conditions.

The following Examples are further illustrative of the present invention. The specific ingredients and processing parameters are presented as being typical, and various modifications can be derived in view of the foregoing disclosure within the scope of the invention.

EXAMPLE I

This Example illustrates the preparation of ethyl 2,2-dimethyl-3-hydroxy-3-(3'-methoxy-4'-hydroxyphenyl)propanoate.

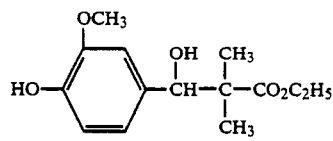

To a solution of lithium diisopropylamide (72.4 mmoles) in 150 mL of tetrahydrofuran at −78° C. and under nitrogen was added ethyl isobutyrate (7.63 g, 65.7 mmoles) in 10 mL of tetrahydrofuran. The solution was stirred for 15 minutes followed by addition of vanillin (5.0 g, 32.9 mmoles) in 10 mL of tetrahydrofuran. A precipitate formed, and the resulting mixture was warmed to room temperature and stirred for 2.5 hours. The reaction medium was quenched with saturated aqueous NH₄Cl and extracted with ethyl ether. The combined ether extracts were washed with saturated aqueous NH₄Cl and saturated aqueous NaCl, dried over anhydrous MgSO₄, and the solvent was evaporated under reduced pressure.

The crude product was purified by chromatography on silica gel and eluted with chloroform. This was followed by high pressure liquid chromatography on silica gel using 20% ethyl acetate in hexane to afford 1.2 g (14%) of pure product as an oil. NMR and IR spectra confirm the title compound structure.

Anal. calc. for $C_{14}H_{20}O_5$: C,62.67; H,7.51
Found: C,62.96; H,7.60

EXAMPLE II

This Example illustrates the preparation of ethyl 2,2-dimethyl-3-hydroxy-3-(3'-ethoxy-4'-hydroxyphenyl)propanoate.

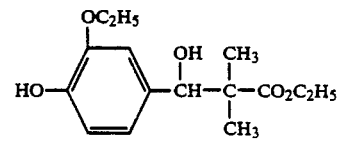

To a solution of lithium diisopropylamide (100 mmoles) in ether (250 mL) and hexane (40 mL) at −78°

C. and under nitrogen was added a solution of ethyl isobutyrate (11.6 g, 100 mmoles) in ether (50 mL) over a period of 5 minutes, and the resulting solution was stirred at −78° C. for 30 minutes. A solution of ethylvanillin (8.3 g, 50 mmoles) in tetrahydrofuran (30 mL) was added. A white precipitate formed, and the mixture was warmed to room temperature and stirred for 18 hours. The mixture was cooled to 0° C., and 100 mL of 1 N HCl were added. The organic layer was washed with water, dried over anhydrous $Na_2SO_4$, and evaporated to give 15.1 g of an oil. The oil was washed with hexane to provide a small amount of residual thick oil. A sample of the crude product (0.90 g) was separated on a dry silica gel column to yield an oil product (0.71 g). NMR and IR spectra confirm the title compound structure.

Anal. calc. for $C_{15}H_{22}O_5$: C, 63.81; H,7.85
Found C, 64.03; H,7.97

EXAMPLE III

This Example illustrates the preparation of ethyl 3-hydroxy-3-(4'-hydroxy-3'-methoxyphenyl)-2-phenylpropanoate.

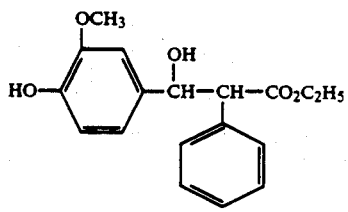

To a solution of lithium diisopropylamide (72.4 mmoles) in 150 mL tetrahydrofuran at −78° C. was added 10.78 g (65.7 mmoles) of ethyl phenylacetate in 10 mL of tetrahydrofuran. The solution was stirred for 15 minutes followed by addition of vanillin (5.0 g, 32.9 mmoles) in tetrahydrofuran. A precipitate formed, and the resulting mixture was warmed to room temperature and stirred for 2.5 hours. The reaction medium was quenched with saturated aqueous $NH_4Cl$ and extracted with ethyl ether. The combined ether extracts were washed with saturated aqueous $NH_4Cl$, and saturated aqueous NaCl, and dried over anhydrous $MgSO_4$. The solvent was evaporated under reduced pressure, and low boiling impurities were removed by Kugelrohr distillation (68° C./0.05 mm Hg). The product was purified by flash chromatography on silica gel and eluted with hexane to 40% ethyl acetate in hexane. A 1.0 g (10%) sample of pure product was obtained as an oil, and the product solidified on standing. NMR and IR spectra confirm the title compound structure.

Anal. calc. for $C_{18}H_{20}O_5$: C,68.34; H,6.37
Found: C,67.97; H,6.45

EXAMPLE IV

This Example illustrates the preparation of ethyl 3-(4'-benzyloxy-3'-methoxyphenyl)-3-hydroxy-2-phenylpropanoate intermediate, and its conversion to the corresponding 4'-hydroxy product.

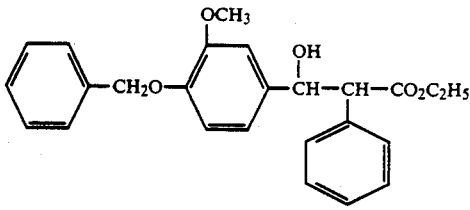

A.

A 5-liter 3-necked round-bottomed flask equipped with a mechanical stirrer, an addition funnel and a thermometer, and cooled in a dry ice/acetone bath and maintained under an atmosphere of nitrogen, was charged with 2 liters of tetrahydrofuran and 208 mL of diisopropylamine (150 g, 1.5 moles). The mixture was cooled to −60° C., and 500 mL of a 2.5 M solution of n-butyllithium (1.25 moles) was added via the addition funnel over a 20 minute period. After the addition of n-butyllithium was completed, the mixture was cooled to −70° C. and 193 g (1.2 moles) of ethyl phenylacetate was added over a 25 minute period. The reaction was stirred for 30 minutes at −70° C., and then allowed to warm to −20° C. over a 30 minute period. A solution of 4-benzyloxy-3-methoxybenzaldehyde (242 g, 1 mole) in 300 mL of tetrahydrofuran was added over a period of 20 minutes, while the temperature was maintained at −20° C. to −25° C. The mixture was stirred at −20° C. for one hour, and then cooled to below −60° C. Glacial acetic acid (170 g, 2.8 moles) was added in one portion. The cooling bath was removed, water (340 mL) was added, and the mixture was stirred vigorously for 5 minutes. The organic layer was separated and washed with water, saturated sodium bicarbonate solution (100 mL), again with water (500 mL), twice with a saturated sodium chloride solution, and then was dried with anhydrous magnesium sulfate.

Analysis of the product solution by HPLC indicated the following composition: ethyl phenylacetate (5%), benzyl vanillin (1%), and the two diastereomers of the product (35% and 59%), thus indicating that the reaction was almost quantitative.

A small sample of the solution was separated by HPLC to yield the two diastereomers. NMR and IR of both confirm the title compound structure.

To a solution of the title compound (176 g) in tetrahydrofuran (500 mL) was added 5 g of 10% Pd/C. The mixture was placed in a 2 liter thick wall round-bottom flask attached to an atmospheric hydrogenation system. Under vigorous stirring, the initial hydrogen uptake was 500 mL per hour. After an uptake of 1 liter of hydrogen, 5 g of fresh catalyst was added and the rate of hydrogen uptake rate was increased to 2 liters per hour. A total of 12 liters of hydrogen were consumed.

Analysis of this solution by HPLC indicated the following composition: ethyl phenylacetate (4%), and the two diastereomers of the product (40% and 56% respectively).

The catalyst was filtered through a bed of celite over a 0.45 nm membrane to provide a clear light yellow solution. The solvent was removed by rotary evaporation, and the residue was dissolved in 150 mL of ethyl acetate while being heated in a water bath. Hexane (300 mL) was added. Upon cooling of the reaction medium, a white precipitate formed. The solid was filtered and washed with a 20% ethyl acetate/hexane solution to yield pure product (127 g, 93%). HPLC of the product indicated a 41:59 ratio of the two diastereomers. NMR and IR spectra confirm the structure of the 4'-hydroxy product.

Anal calc. for $C_{18}H_{20}O_5$: C,68.34; H,6.37
Found: C,68.18; H,6.34

A pure sample of each of the two diastereomers was obtained by both preparative HPLC and fractional crystallization. NMR and IR spectra confirm the structure of the diastereomers, which had melting points of 112°–114° C and 212°–114° C., respectively. TGA and pyrolysis GC-MS for both diastereomers were essentially identical, indicating that both had very similar thermal properties.

EXAMPLE V

This Example illustrates the preparation of ethyl 3-hydroxy-3-[3'-methoxy-4'-(tetrahydropyran-2-yloxy)-phenyl]-2-phenylpropanoate intermediate, and its conversion to the corresponding 4'-hydroxy product.

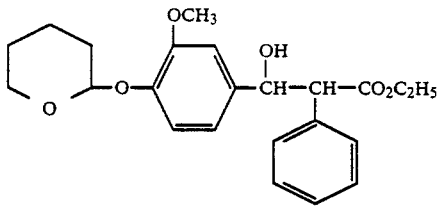

A.

To a solution of lithium diisopropylamide (0.1 mole) in ether (300 mL) and hexane (40 mL) at −78° C. and under nitrogen was added with stirring a solution of ethyl phenylacetate (16.4 g, 0.1 mole) in ether (100 mL) over a 20 minute period, and was left stirring at −78° C. for 30 minutes. A solution of tetrahydropyran-2-yl-protected vanillin (23.6 g, 0.1 mole) in ether (150 mL) was added over a period of about 30 minutes, and the solution was warmed to room temperature. Water (200 mL) was added, and the organic layer was separated, washed with water and dried over anhydrous $Na_2SO_4$. Evaporation of the solvent provided 39.2 of an oil. The above crude oil was separated by flash chromatography on a silica-gel using hexane/acetone (85:15) as the eluant. The pure product (16.5 g, 41.3%) was obtained as an oil. NMR and IR confirmed the title compound structure, and indicated that the product was a mixture of two diastereomers.

To a solution of the title compound (24.0 g) in 400 mL of 95% EtOH was added 15 drops of 5% HCl solution to provide a pH of 3. After a reaction period of 3.5 hours at room temperature, water (500 mL) was added to the solution and the reaction product was extracted with ether. The organic layer extract was washed with water, dried over anhydrous $Na_2SO_4$, and evaporated under reduced pressure to a residual product (17.2 g). Recrystallization of the crude product from hexane-ethyl acetate yielded 14.9 g (78.6%) of the pure product as a mixture of diastereomers. NMR and IR spectrum confirmed the structure of the 4'-hydroxy product.

EXAMPLE VI

This Example illustrates the preparation of ethyl 3-hydroxy-3-(3'-methoxy-4'-trimethylsilyloxyphenyl)-2-phenylpropanoate, and its conversion to the corresponding 4'-hydroxy product.

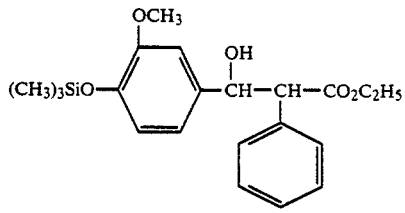

The reaction of ethyl phenylacetate (69 g, 0.42 mole) with 78.4 g (0.35 mole) of 3-methoxy-4-trimethyl-silyloxy-benzaldehyde was conducted in the manner described in Example IV, and 151 g of crude product was isolated as an oil. HPLC indicated that the material was the title product as a mixture of two diastereomers, and trace amounts of unreacted aldehyde and the unreacted excess ester. NMR and IR spectra confirm the title compound structure.

B.

To a solution of the title compound (1 g) in tetrahydrofuran (5 mL) was added 1 mL of 5% HCl solution with vigorous stirring, and after 1 hour HPLC indicated complete hydrolysis of the title compound. NMR and IR spectra confirmed the structure of the 4'-hydroxy product.

EXAMPLE VII

This Example illustrates the preparation of ethyl 3-(4'-ethoxymethoxy-3'-methoxyphenyl)-3-hydroxy-2-phenylpropanoate, and its conversion to the corresponding 4'-hydroxy product.

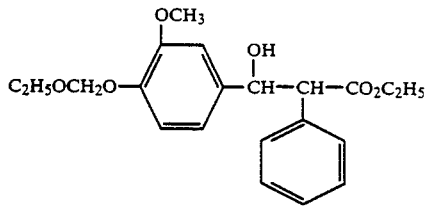

The reaction of ethyl phenylacetate with 4-ethoxymethoxy-3-methoxybenzaldehyde was conducted on a 0.1 mole scale employing the procedure described in Example IV. The recovered product was a mixture of diastereomers.

B.

To a solution of the title compound (5 g) in tetrahydrofuran (50 mL) was added 3 mL of 5% HCl solution. After 3 hours at room temperature the product was isolated and found to be identical with an authentic sample of the 4'-hydroxy product by NMR, IR and HPLC.

What is claimed is:

1. A smoking composition comprising an admixture of combustible filler selected from natural tobacco, reconstituted tobacco and tobacco substitutes, and (2) between about 0.0001–5 weight percent, based on the total weight of filler, of a flavorant-release additive corresponding to the formula:

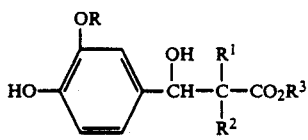

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

2. A smoking composition in accordance with claim 1 wherein the flavorant-release additive is ethyl 2,2-dimethyl-3-hydroxy-3-(3'-methoxy-4'-hydroxyphenyl)propanoate.

3. A smoking composition in accordance with claim 1 wherein the flavorant-release additive is ethyl 2,2-dimethyl-3-hydroxy-3-(3'-ethoxy-4'-hydroxyphenyl)propanoate.

4. A smoking composition in accordance with claim 1 wherein the flavorant-release additive is ethyl 3-hydroxy-3-(4'-hydroxy-3'-methoxyphenyl)-2-phenylpropanoate.

5. A cigarette smoking product comprising (1) a combustible filler selected from natural tobacco, reconstituted tobacco and tobacco substitutes, and (2) a paper wrapper which has incorporated therein a flavorant-release additive corresponding to the formula:

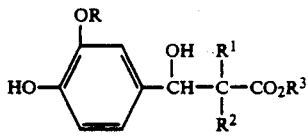

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

6. A cigarette smoking product in accordance with claim 5 wherein the paper wrapper contains between about 0.01–5 weight percent of flavorant-release additive.

7. A cigarette smoking product in accordance with claim 5 wherein the flavorant-release additive in the paper wrapper is ethyl 2,2-dimethyl-3-hydroxy-3-(3'-methoxy-4'-hydroxyphenyl)propanoate.

8. A cigarette smoking product in accordance with claim 5 wherein the flavorant-release additive in the paper wrapper is ethyl 2,2-dimethyl-3-hydroxy-3-(3'-ethoxy-4'-hydroxyphenyl)propanoate.

9. A cigarette smoking product in accordance with claim 5 wherein the flavorant-release additive in the paper wrapper is ethyl 3-hydroxy-3-(4'-hydroxy-3'-methoxyphenyl)-2-phenylpropanoate.

10. A cigarette smoking product in accordance with claim 5 wherein the combustible filler contains between about 0.0001–5 weight percent, based on the weight of filler, of a flavorant-release additive corresponding to the formula:

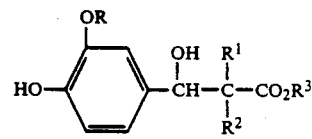

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_{1-4}$ alkyl or $C_6$–$C_{10}$ aromatic substituent.

11. A cigarette smoking product in accordance with claim 10 wherein the flavorant-release additive in the combustible filler is ethyl 2,2-dimethyl-3-hydroxy-3-(3'-methoxy-4'-hydroxyphenyl)propanoate.

12. A cigarette smoking product in accordance with claim 10 wherein the flavorant-release additive in the combustible filler is ethyl 2,2-dimethyl-3-hydroxy-3-(3'-ethoxy-4'-hydroxyphenyl)propanoate.

13. A cigarette smoking product in accordance with claim 10 wherein the flavorant-release additive in the combustible filler is ethyl 3-hydroxy-3-(4'-hydroxy-3'-methoxyphenyl)-2-phenylpropanoate.

14. Ethyl 2,2-dimethyl-3-hydroxy-3-(3'-methoxy-4'-hydroxyphenyl)propanoate.

15. Ethyl 2,2-dimethyl-3-hydroxy-3-(3'-ethoxy-4'-hydroxyphenyl)propanoate.

16. Ethyl 3-hydroxy-3-(4'-hydroxy-3'-methoxyphenyl)-2-phenylpropanoate.

17. Ethyl 3-(4'-benzyloxy-3'-methoxyphenyl)-3-hydroxy-2-phenylpropanoate.

18. Ethyl 3-hydroxy-3-[3'-methoxy-4'-(tetrahydropyran-2-yloxy)phenyl]-2-phenylpropanoate.

19. Ethyl 3-hydroxy-3-(3'-methoxy-4'-trimethylsilyloxy)phenyl-2-phenylpropanoate.

20. Ethyl 3-(4'-ethoxymethoxy-3'-methoxyphenyl)-3-hydroxy-2-phenylpropanoate.

21. A process for preparing a β-hydroxyester corresponding to the formula:

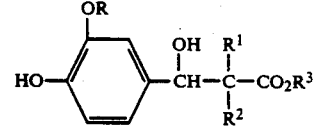

which comprises (1) condensing the following reactants under Claisen condensation conditions in an organic solvent medium:

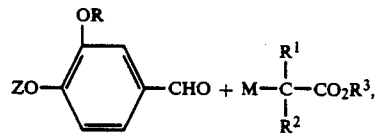

to form an intermediate corresponding to the formula:

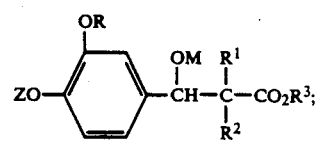

and (2) converting the —OZ and —OM substituents to hydroxyl groups by hydrolysis or hydrogenolysis means; wherein in the above represented formulae R is methyl or ethyl; $R^1$ is hydrogen or a $C_1-C_4$ alkyl substituent; $R^2$ is hydrogen or a $C_1-C_4$ alkyl or $C_6-C_{10}$ aromatic substituent; $R^3$ is a $C_1-C_{10}$ alkyl or $C_6-C_{10}$ aromatic substituent; M is a monovalent metal atom which is displaced by hydrogen under acidic hydrolysis conditions; and Z is a $C_1-C_{10}$ organic radical which is displaced by hydrogen under hydrogenation or acidic hydrolysis conditions.

22. A process in accordance with claim 21 wherein the condensation reaction in step(1) is conducted at a temperature in the range between about −80° C. and 50° C., and after completion the reaction medium is quenched with an acid reagent.

23. A process in accordance with claim 21 wherein M in the formulae is a lithium, sodium or potassium metal atom.

24. A process in accordance with claim 21 wherein Z in the formulae is a benzyl radical.

25. A process in accordance with claim 21 wherein Z in the formulae is a tetrahydropyran-2-yl radical.

26. A process in accordance with claim 21 wherein Z in the formulae is a trimethylsilyl radical.

27. A process in accordance with claim 21 wherein Z in the formulae is an ethoxymethyl radical.

* * * * *

UNITED STATES PATENT OFFICE
CERTIFICATE OF CORRECTION

Patent No. 5,129,954          Dated July 14, 1992

Inventor(s) Chan et al

It is certified that error appears in the above-identified patent and that said Letters Patent is hereby corrected as shown below:

Col. 10, line 64, insert --(1)-- before "combustible".

Col. 13, line 4, "$C_1-C_{10}$" should be $C_1-C_4$--.

Col. 4, line 65, "above:" should be --above--.

Col. 5, line 25, "substituted" should be --substituent--.

Col. 8, between lines 48 and 49, insert --B.-- as a heading.

Col. 9, between lines 52 and 53, insert --B.-- as a heading.

Col. 10, between lines 13 and 14, insert --A.-- as a heading.

Signed and Sealed this

Twenty-first Day of September, 1993

Attest:

BRUCE LEHMAN

Attesting Officer          Commissioner of Patents and Trademarks